United States Patent
Manka et al.

(10) Patent No.: US 8,717,565 B2
(45) Date of Patent: May 6, 2014

(54) OPTICALLY ACTIVE FUNCTIONAL FLUID MARKERS

(75) Inventors: John S. Manka, Chardon, OH (US); Ying Wang, Hudson, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 120 days.

(21) Appl. No.: 13/139,362

(22) PCT Filed: Dec. 10, 2009

(86) PCT No.: PCT/US2009/067421
§ 371 (c)(1),
(2), (4) Date: Aug. 23, 2011

(87) PCT Pub. No.: WO2010/077754
PCT Pub. Date: Jul. 8, 2010

(65) Prior Publication Data
US 2011/0292388 A1     Dec. 1, 2011

Related U.S. Application Data

(60) Provisional application No. 61/138,264, filed on Dec. 17, 2008.

(51) Int. Cl.
*G01J 4/00* (2006.01)
(52) U.S. Cl.
USPC .......................................... 356/364
(58) Field of Classification Search
USPC .......................................... 356/364
See application file for complete search history.

(56) References Cited

U.S. PATENT DOCUMENTS

| 606,043 | A | * | 6/1898 | Hayden et al. | 340/815.69 |
|---|---|---|---|---|---|
| 2,861,493 | A | * | 11/1958 | Landegren | 356/367 |
| 3,724,952 | A | | 4/1973 | Vossberg | |
| 5,145,573 | A | | 9/1992 | Riedel et al. | |
| 5,429,952 | A | * | 7/1995 | Garner et al. | 436/518 |
| 5,942,444 | A | | 8/1999 | Rittenburg et al. | |
| 5,956,144 | A | * | 9/1999 | Kaplan et al. | 356/364 |
| 2005/0094144 | A1 | | 5/2005 | Gibbs et al. | |
| 2009/0009764 | A1 | * | 1/2009 | Slepicka | 356/370 |
| 2009/0050809 | A1 | * | 2/2009 | Holec | 250/343 |

FOREIGN PATENT DOCUMENTS

| DE | 10244306 A1 | 4/2004 |
|---|---|---|
| WO | 02/18915 | 3/2002 |
| WO | 03078551 | 9/2003 |

OTHER PUBLICATIONS

Corresponding PCT Publication No. WO 20120/077754 A1 and PCT Search Report published Jul. 8, 2010.

* cited by examiner

*Primary Examiner* — Tarifur Chowdhury
*Assistant Examiner* — Abdullahi Nur
(74) *Attorney, Agent, or Firm* — Christopher D. Hilker

(57) ABSTRACT

The present invention relates to a method of identifying in a fluid by measuring the amount of optical rotation the fluid causes in a beam of polarized light. The invention further provides for the use of an optional optically active marker in the fluids in order the impact the amount of rotation the fluid will cause. The invention provides a convenient and reliable means for identifying the fluid before, during and/or after the fluid's use.

6 Claims, No Drawings

OPTICALLY ACTIVE FUNCTIONAL FLUID MARKERS

FIELD OF THE INVENTION

The present invention relates to the determination of the identity of a fluid, such as organic fluids. In particular, the invention provides a convenient and reliable means for identifying the fluid before, during and/or after the fluid's use. The present invention also relates to a system for identifying a fluid by passing a beam of polarized light through a sample of the fluid, and measuring the amount of optical rotation caused by the sample. The invention further provides for the use of optically active markers to increase and/or adjust the amount of rotation that is observed from a sample. The measurement of this rotation, caused by the materials in the fluid being tested, including the optional optically active marker, allows for the identification of the fluid.

BACKGROUND OF THE INVENTION

Various types of fluids are used in numerous and very different applications. In all of the varied types of and uses for fluids, there is often a need to identify a fluid and/or the source of the fluid and a need for the means of identifying the fluid to be convenient and reliable.

Functional fluids, as defined in this application, are fluids employed in a variety of automotive, off-highway vehicles, on-highway vehicles, equipment, machines, metal working and industrial applications. It is important to know the identity of such functional fluids to prevent the improper utilization or unauthorized counterfeiting of the functional fluid. A proper functional fluid helps to insure the good condition of the device and/or equipment containing the functional fluid and may also impact warranty agreements. It is, therefore, desirable to be able to determine the identity of such functional fluids.

Methods exist for the analysis and identification of fluids using various reagents in determining the presence and/or concentration of various constituents of the fluids. Specific reagents may be employed for determining the presence and concentration of components in functional fluids. These methods generally analyze for pH, coloring agents, and contaminants using reactive reagents on test strips. These methods also generally require controlled conditions for the reactive reagents to function properly. Further, these methods may be subjective and inaccurate.

Markers have been used to identify fluids. Proton accepting chemical substances have been proposed as markers, or taggants, especially for petroleum-derived fuels. The marker is dissolved in a liquid to be identified, and then subsequently detected by performing a chemical test on the marked liquid. Markers are sometimes employed by government agencies to ensure appropriate taxes have been paid on particular grades of fuel. Oil companies also mark their products to help assist in identifying diluted or altered products. These companies often go to great expense to make sure their branded products meet certain specifications as well as to provide their products with effective additive packages. Consumers rely upon product names and quality designations to assure that the product being purchased is the quality desired. Thus, it is important to be able to identify a marker in a petroleum product.

Traditionally, the presence of a marker substance is detected and optionally quantified by extracting the fluid with an aqueous or significantly aqueous solution of an acid substance, the precise nature of which can be varied depending on the marker substance. The acid reacts with the marker compound to produce a readily visible, more or less intensely colored cation dissolved in the aqueous acid phase. This method is disclosed in U.S. Pat. No. 5,145,573. Additionally, a method has been disclosed in WO 03/078551 A2 where the acidic substance has been applied to a test strip. The test strip is dipped into the oil and a diazo-type marker reacts with the acidic substance in the test strip and changes color.

In many of these methods it may be necessary to make repeated, typically two or three, extractions of the fluid to recover a sufficient amount of marker in order for complete quantification. Additionally, the extracted, separated phase is often classifiable as a hazardous waste and presents problems of safe and lawful disposal, especially when examinations are made "in the field." Furthermore, the functional fluid being tested may be contaminated by the process, making its return to its original source undesirable, presenting additional waste disposal problems.

Many owners/users of, operators of equipment that depend on, and/or retailers of these fluids currently depend on off-site labs to determine the specific identify of a fluid when such questions arise, such as in warranty resolutions. A tool that would allow identification of a fluid in the field would speed warranty resolution and similar issues.

It is an object of this invention to provide an easy and convenient delivery system to accurately analyze the identity of a fluid. It is a further object of the invention to provide a method to analyze functional fluids rapidly in the field. It is still the object of the present invention to provide a method to test the identity of a functional fluid in the field rapidly by untrained personnel and without precision measurement. It is still a further object of the invention to provide a diagnostic kit for identification of functional fluids rapidly in the field.

SUMMARY OF THE INVENTION

The present invention provides a method to determine the identity of a functional fluid comprising: (1) adding an optional optically active marker component to the fluid; (2) obtaining a sample of the fluid before, during or after its use in an application; (3) passing a beam of polarized light through the sample; (4) measuring the rotation of the plane of the light after it passes through the sample; (5) determining the identity of the fluid by the amount of rotation observed.

The invention further provides for the use of chiral molecules as optically active markers where the chiral molecules are at least partially soluble in the fluid. The optically active marker components used in the methods of the invention are non-racemic in regards to at least one set of enantiomers.

The invention further provides a diagnostic kit for the analysis of a fluid comprising a source of polarized light, a means for directing a beam of polarized light from said source through a sample of fluid, a means for detecting the amount of rotation in the beam of polarized light after it passes through the sample, and a means of communicating the results from the analyzer to a user. The kit may also comprise written instruction, pictures, drawings, and/or photographs to aid the user in the identification of the fluid. The fluid used with such diagnostic kits may comprise an optically active marker.

DETAILED DESCRIPTION OF THE INVENTION

The invention provides for the use of measured optical rotation as a means for identifying and/or confirming the source of a fluid, including a method and a device, such as a kit, for analyzing and monitoring the identity of various fluids. The invention further provides optical markers which impact a fluid's ability to rotate polarized light. These markers may be used in the methods, devices and kits described here, used in identifying and/or confirming the source of a fluid and/or monitoring the identity of a fluid.

Fluids to be Identified

The fluids that are suitable for use in the present invention, in that the methods and optically active markers described herein may be used to identify said fluids, are not overly limited. In general, the methods and optically active markers described herein may be used in any liquid or fluid for which there is a need to confirm and/or determine the fluid's source and/or identity. More particularly, the methods of the invention are directed toward functional fluids such as lubricants and fuels and industrial fluids.

Suitable fluids include, for example, functional fluids which come from innumerable sources, including internal combustion engines, stationary engines, turbines, transmissions, differentials, pumps, metalworking operations, cooling systems, industrial systems and the like. The functional fluids include automatic transmission fluids, continuously variable transmission fluids, infinitely variable transmission fluids, traction drive transmission fluids, manual transmission fluids, power steering fluids, antifreeze fluids, lubricating oils, greases, crankcase lubricants, cylinder lubricants, mineral oils, Group I, II, III or IV base oils, differential lubricants, turbine lubricants, gear lubricants, gear box lubricants, axle lubricants, farm tractor fluids, transformer fluids, compressor fluids, cooling system fluids, metal working fluids, hydraulic fluids, brake fluids, industrial fluids, fuels, infinitely variable transmission fluid, and the like. In one embodiment, the functional fluid is an automatic transmission fluid. In one embodiment, the functional fluid is a power steering fluid. In one embodiment, the functional fluid is an internal combustion fuel such as gasoline and/or diesel. In one embodiment, the functional fluid is compressor fluids such as air compressor lubricants and/or turbine lubricants. In one embodiment, the functional fluid is an internal combustion engine oil. In one embodiment the functional fluid is tested after some time in use, up to and including the fluid's service life.

In some embodiments the fluids are organic and are free of any aqueous materials except small amounts that are commonly caused by contamination. In such embodiments the fluid may contain less than 10% water or less than 5%, less than 1% or even less than 0.5% water. In other embodiments, the fluids include both organic and aqueous fluids, and mixtures thereof.

Non-fluid materials may also be used with the invention, where the non-fluid material is dissolved into a solvent, melted, or otherwise transferred into a fluid medium in order to be tested.

Many fluids contain materials that will rotate the plane of polarized light. The measurement of this rotation may be used to verify the identity of the fluid, as described below. Such materials inherently contain optically active materials that may be used as markers in the methods of the invention. The invention includes methods that measure the optical rotation of such materials and uses the observed rotation as a means to identify the fluid. In some embodiments, a fluid may not provide any significant rotation and/or may not rotate light any more or less than a competing, counterfeit and/or alternative product. In such cases the invention further provides for the use of optically active markers which may be added to the fluid in order to provide a different level of optical rotation. The fluid, which then includes the optional marker, can then be tested by the methods of the present invention and the observed optical rotation, which has been adjusted by the use of the optical markers described herein, may be used to identify and/or verify the identify of the fluid Solvents to be Used with the Markers In the embodiments where optical markers are added to the fluid, the markers may be added to the fluid with which they are used as a neat component. In other embodiments the marker may be present in a mixture comprising one or more optical markers, as described herein, and further comprising one or more solvents, forming a marker concentrate or marker solution, which may then be added to the fluid. This mixture may further comprise additional materials, such as but not limited to, performance additives designed to impact and/or improve the performance of the resulting functional fluid.

As described above, suitable solvents may be used with the markers, forming a marker solution. The solvent used depends on the type of functional fluid being tested, the delivery system being used and the marker being used. Combinations of solvents are also useful when the marker, depending on the application and type of analysis desired, is not soluble in the functional fluid. Solvents or combinations of solvents may be selected by considering desirable properties including good solvency power and miscibility with the functional fluid and the marker, low vapor pressure at ambient temperatures, high flash points and the like.

Suitable solvents include aliphatic, unsaturated and aromatic hydrocarbons, alcohols, glycols, glycol ethers, polyols such as glycerol, lower alcohols, such as methanol, ethanol and propanol, ethers, esters, amides, amines, water and the like. Combinations of solvents may be used.

In some embodiments the marker component, which refers to the mixture of the marker and any optional solvents and/or additional additives that may be present, is free of any materials that would inhibit the optically active nature of the marker compounds. In other embodiments the marker component is free of any materials that would react with the optically active markers present. In other embodiments the marker component is free of any non-chiral and/or non-optically active components.

It is understood that the term marker and/or the term marker component, when used in the application, unless otherwise indicated, can mean either the marker compound or compounds themselves with no added solvent, or the marker solution comprising a mixture of the marker compound or compounds and one or more solvents or additional additives. The solvent may be present in the marker solution in the range of about 1 wt. % to about 99.99 wt. %, in one embodiment about 5 wt. % to about 98 wt. % and in another embodiment about 1 wt. % to about 95.5 wt. % of the marker solution.

The Optically Active Markers

The marker substance is chosen to be compatible with, or not adverse to, the fluid with which it is used and/or the system in which the fluid will be used. In one embodiment, the marker is chosen to survive the application and/or service conditions the functional fluid is exposed to during its use.

In one embodiment, the marker substance is used to identify new and/or unused fluids. In other embodiments it is useful to validate the identity of a used fluid for, as an example, warranty claims. In this case the marker needs to survive and be detectable after experiencing the typical operating and/or use conditions of the fluid. In the case of functional fluids, this may include surviving the operation of an engine or other device in which the functional fluid is used.

Markers suitable for use in the present invention may be described as optically active markers. Suitable optically active markers include: one or more compounds comprising chiral molecules; one or more compounds wherein its molecules contains at least one chiral center, axis or plane; one or more compounds wherein its molecules contains at least one tetrahedrally-bonded atom in which all four substituents on the tetrahedrally bonded atom are different; or mixtures of one or more of the compounds described above. In all of the embodiments described above, the mixture of markers used must have an overall enantiomeric excess such that an optically active system exists, such that the system rotates the plane of polarized light.

In one embodiment, the marker of the present invention includes one more compounds represented by Formula I shown below:

Formula I wherein X is C, N, P, or S; and $R^1$, $R^2$, $R^3$, and $R^4$ are each independently a hydrocarbyl group, an —$OR^5$ group where $R^5$ is hydrogen or a hydrocarbyl group, an aromatic group, a lone pair of electrons, a double bonded oxygen or nitrogen atom when X is P or S, with the provisos that each R group is unique and each R group may contain functional groups. That is $R^1$, $R^2$, $R^3$, and $R^4$ are each a unique substituent group wherein $R^1 \neq R^2 \neq R^3 \neq R^4$.

In some embodiments, the optically active marker is: soluble in the fluid being marked; exhibits a measurable optical rotation of an appropriate wavelength of light; causes no harm to the fluid being marked or to the application in which the fluid is used; is colorless in the visible spectrum and/or makes no impact on the color of the fluid being marked; is odorless and/or tasteless and/or has no impact on the odor and/or taste of the fluid being marked; or some combination thereof.

The markers may be soluble in the fluid from 0.00001% up to 100% by weight. Appropriate wavelengths of light for which suitable markers cause rotations include ultraviolet light, visible light, infrared light, or combinations thereof. Sufficient optical rotation may be an amount greater than the margin of error in the measuring device used to evaluate the rotation, and in some embodiments is at least 0.1 degree of rotation, at least 0.5 degrees, at least 1 degree, or at least 5 degrees of rotation. Optical rotations of greater than 360 degrees are possible but for this invention molecules that rotate light greater than 360 degrees are characterized as having optical rotations of their actual rotation minus 360.

A compound is considered to be optically active if it can rotate the plane of polarized light that passes through it. The amount of optical rotation is determined by the molecular structure and concentration of the optically active molecules in the fluid, the wavelength of the light passing though the fluid, the optical path length involved, and the temperature. Each optically active substance provides its own specific rotation as defined in Biot's law:

$$[\alpha]_\lambda^T = \frac{\alpha_\lambda^T}{c \cdot l}$$

where [α]=specific rotation, T=temperature, λ=wavelength, α=optical rotation, c=concentration in g/100 ml, l=optical path length in dm. The rotation caused by the optically active compounds results from the interaction of chiral materials with polarized light. Specific enantiomers of a chiral molecule absorb polarized light to differing degrees. Enantiomers can be named by the direction in which it rotates the plane of polarized light. If it rotates the light clockwise (as seen by a viewer towards whom the light is traveling) the enantiomer is labeled (+) or "d-" for dextrorotatory. Its mirror-image is labeled (−) or "l-" for levorotatory.

Optically active compounds may also be labeled by identifying each isomer by the spatial configuration of its atoms using an R/S designation. The R/S system has no fixed relation to the (+)/(−) or d-/l-systems described above. The R/S system labels each chiral center present in a compound with an R or S according to a system in which the chiral center's substituents are assigned a priority, based on atomic number. If the chiral center is oriented such that the lowest-priority substituents is pointed away from a viewer, the viewer will then see two possibilities: if the priority of the other three substituents decreases in a clockwise direction, it is labeled R for Rectus; if the substituents' priority decrease in a counter-clockwise direction, it is labeled S for Sinister. This system labels each chiral center (and/or each chiral plane, chiral axis, and/or chiral group) in a molecule and so has greater generality than the other systems described above.

Optically active compounds include chiral molecules. The term chiral is used to describe an object that is non-superimposable on its own mirror image. Chiral molecules can have "point chirality" where the chirality of the molecule is centered around a single atom, usually a carbon atom, which has four different substituents. If all four substituents on the tetrahedrally bonded atom are different, the molecule is chiral. Isotopic differences are enough for chirality.

The above definition for chiral molecules is not limited to tetrahedral carbon atoms, but also includes any other type of central atom with an appropriate set of substituent groups or ligands. Examples include octahedral and other coordination geometries of appropriate substitution, including metal complexes and inorganic structures. In addition, a molecule may have multiple chiral centers. It is also possible for a molecule to be chiral without having point chirality. Common examples include 1,1'-bi-2-naphthol (BINOL) and 1,3-dichloro-allene, which have axial chirality, and (E)-cyclooctene, which has planar chirality.

The stereogenic center of a chiral molecule need not to be located on a specific atom. For example, adamantane derivatives with suitable substituents may also be chiral. In these structures an entire group, as opposed to a single atom, holds four substituents in a spatial arrangement making the compound non-superimposable on its mirror image.

There are many examples where chirality of molecules results from hindered rotation of groups or spatial arrangements of chemical moieties, a few examples of which include 1,2,3,4-tetramethyl-cyclooctatetraene, 2,5-dimethyl-bicyclo-2,2,2-oct-2,5,7-triene, and perchloro-triphenylamine. In addition, catenanes and molecular knots made up from achiral molecules may be chiral.

A chiral substance is considered enantiopure or homochiral when only one of two possible enantiomers is present. A mixture of equal amounts of the two enantiomers is said to be a racemic mixture. A chiral substance is enantioenriched or heterochiral when an excess of one enantiomer is present but not to the exclusion of the other. Enantiomeric excess is a measure for how much of one enantiomer is present compared to the other. A non-racemic chiral mixture may also be called scalemic.

In some embodiments, the present invention uses one or more optically active markers where the marker component and/or mixture is not a racemic mixture. That is, the marker component is scalemic and has an enantiomeric excess, or has less than 100% optical purity. In some embodiments, the present invention requires the mixture of optically active markers to contain at least a 5 percent by weight excess of one enantiomer for each optically active marker present. In still other embodiments the excess must be 20 percent by weight, 50 percent by weight or even 75 percent by weight.

The markers of the present invention may include one or more of the following: Abscisic Acid, sulfoximes, sulfonamides, sultams, 1-Acetoxychavicol Acetate, Acenaphthenol, Alfuzosin, Alprenolol, Althiazide, 1-Aminoindan, Amlodipine, Anisoin, 9-anthrylethanol, 9-anthryl trifluoromethyl carbinol, Arginine, Atenolol, Atropine, Azelastine, Bambuterol, Bendroflumethiazide, Benzoin, 1-(4-Benzyloxy) phenyl, Ethanol, Beta Naphthyl Methyl Carbinol, Betaxolol, Bifonazole, 1,1'-Binaphthol Monomethylether, 1-(p-Bromophenyl) Ethanol, Brompheniramine, Buckminsterfullerene-Enone [2+2] Photoadducts, Bufuralol, Bupivacaine, Bupranolol, Calanolide, Carazolol, Carprofen, Carvedilol, Chlorflurecol Methyl Chlormezanone, 4-Chloromandelic acid, 2-(2-Chloro-4-methylphenoxy) Propionic Acid, 2-(3-Chlorophenoxy) Propionic Acid, 1-(m-Chlorophenyl) Ethanol, 1-(o-Chlorophenyl) Ethanol, 1-(p-Chlorophenyl) Ethanol, Chlorthalidone, Cicloprofen, Citalopram, Clenbuterol, Cromakalim, Crotoxyphos, Cyclandelate, 1-Cyclohexyl-1-phenylacetic Acid, 1-Cyclopentyl-1-phenylacetic Acid, Cyclopentyl Benzoyl-Diamide, Cyclophosphamide, Cyclothiazide, Cyclothiazide-1, Combretastatin D-1, Coumachlor, Cypermethrin, Devrinol, Napropamide, Dexmedetomidine, 2,2'-Diaminobinaphthalene, 2,3-Dibenzoyl-Tartaric Acid, Diclofop Methyl, Dihydrotetrabenazine, Diltiazem, Dimethyl (1-acetoxy-3-phenyl-E-propenyl) phosphonate, Dimethyl (1-hydroxy-3-phenyl-E-propenyl)phosphonate, 3,5-Dimethylanilide-R,S-Ibuprofen, Dinocap, Diperodon, Diperodon-1, Diperodon-2, Diphenylnitroxide, Disopyramide-1, Disopyramide-2, Ditoluoyltartaric Acid, Dropropizine, Doxazosin, EEDQ, Ethotoin, Ethyl-2-(p-Hydroxyphenoxy) Propionate, Ephedrine, Etodolac, Fenoprofen, Fenoterol, Fenoxaprop-ethyl, Fenvalerate, Flavanone, Flobufen, Flobufen-1,4-Fluorophenylalanine, Fluazifop-butyl, Fluridil, 1-(p-Fluorophenyl) Ethanol, Fluoxetine (Prozac), Flurbiprofen, Formoterol, Glutamine, Glutamic Acid, Haloxyfop-ethoxyethyl, Hanessian's Lignan, Hesperitin, Hesperitin-2, Hexobarbital, Histidine, Homatropine, Homocysteine Thiolactone, Huperzine, Hydratropic Acid, Hydrobenzoin, Hydroxychloroquine, 1-(4-Hydroxyphenyl) Ethanol, p-Hydroxy-Phenylglycine, 2-(4-Hydroxy-Phenoxy) Propionic Acid, Ibuprofen, Ibuprofenol, Idazoxan, Ifenprodil, Ifenprodil-2, Ifosfamide, Indapamide, Indapamide-1, Indoprofen, Ipsdienol, Isoxsuprine, Isradipine, Isradipine-1, Ketamine, Ketoconazole, Ketoprofen, Ketoprofen-1-Naphthylamide, Ketorolac, KP 411, Kynurenine, Lansoprazole, Laudanosine, Leptophos, Phosvel, Leucine, Leucine-1, Lorazepam, Lorglumide, Loxoprofen, Luciferin, Mandelic Acid, McN 5652, Mecoprop, Mephenyloin, Metalaxyl, Methadone, Methadone-1, Methionine, a-Methoxyphenyl Acetic Acid, 2-Methoxyphenyl Phenyl Carbinol, 1-(4-Methoxyphenyl)-2-butanol, 1-(o-Methoxyphenyl) Ethanol, 1-(4-Methoxyphenyl)-2-propanol, Methyl Mandelate, 1-(o-Methylphenyl) Ethanol, 1-(m-Methylphenyl) Ethanol, 1-(p-Methylphenyl) Ethanol, Methyl 3-phenyl-3-azido-2-hydroxypropanoate.

Additional examples of chiral compounds include: 3-Methyl-5-phenylhydantoin, Metolachlor, Metolazone, Metoprolol, Mianserin, Modafinil, Mosapride, Nadifloxacin, Nadolol, 1,1'-bi-2-naphthol, a-naphthol methyl carbinol, 1-Naphthyl-2-butanol, 2-Naphthyl-2-butanol, 1-Naphthylureaphenethylamine, Napropamide, Naproxen Diisopropyl Amide, Naproxen (normal phase), Naproxen (reversed phase), Naproxen (on ULMO CSP), Naproxen Methyl Amide, Naringenin, Nicardipine, N-CBZ-Valine, Nicotine, Nimodipine, Nirvanol, Norleucine, Norvaline, Octopamine, Ofloxacin, Omeprazole, Omeprazole (Prilosec), Omeprazole (Prilosec)-1, Oxazepam, Oxprenolol, Oxybutynin, p-Chloro-Warfarin, Pantoprazole, Pazufloxacin, Permethrin, Pheniramine, Phenyl cyclohexyl Carbinol, 2-Phenylcyclopropane Carboxylate, Phenyl ethyl carbinol, Phenyl Isopropyl Carbinol, Phenyl Methyl Carbinol, 1-[(4-Phenyl)phenyl] Ethanol, Phenyl phenylethyl Carbinol, 1-Phenyl-2-propanol, Phenyl propyl carbinol, Phenyl tribromomethyl carbinol, Phenylalanine, Phenylbutyric acid, Phenylethylene Glycol, Phenylglycine, 1-Phenylpentanol, Phenylsuccinic Acid, Pindolol, Pindolol-1, Pirprofen, PPO Inhibitor, Practolol, Praziquantel, Prilocaine, Proglumide, Proline, Pronethalol, Propafenone, Propiconazole, Tilt, Propranolol, Quizalofop-ethyl, Ranolazine, Rebamipide, Resmethrin, SC 41930, Serine, Sethoxydim, Sotalol, Stilbene Oxide, Styrene Oxide, Sulconazole, Sulfinpyrazone, Sulindac, Sulpiride, Suprofen, Taxifolin, Temazepam, Temazepam-1, Terbutaline, Terfenadine, Terfenadine-2, Tert-butyl-2-(benzamido) Cyclopentyl Carbamat, Separation, Tert Butyl Phenyl Carbinol, Tetrabenazine, Tetrahydrobenzopyrene-7-ol, Tetrahydropalmatine, Tetrahydropalmatine-2, Tetrahydropyrimindine, Tetrahydrozoline, 1,2,3,4-tetrahydro-1-naphtol, 1,2,3,4-tetrahydro-1-naphthylamine, Tetramethrin, Tetramisole, Thalidomide, 2-Thiopheneethanol, 3-Thiopheneethanol, Tiaprofenic Acid, Timolol maleate, Tofisopam, Tolperisone, Trans-2-phenyl-1-cyclohexanol, Trans-11,12-Diamino-9,10-dihydro-9,10-ethanoanthracene, Trichlormethiazide, 4-(Trifluoromethyl)mandelic Acid, 1,1,2-triphenyl-1,2-ethanediol, 1,3,5-triphenylpent-4-yn-1-one, 1-(m-Trifluoromethylphenyl) Ethanol, a-Trityl-2-naphthalene propionic acid, Troger's Base, Troglitazone, Trolox, Trolox-1, Trolox-methylether, Tropicamide, Tryptophan, Tulobuterol HCl, Tyrosine, U-100057, U-94863, trans-U-50488H, Valine, Vanilmandelic Acid, Vapol, Verapamil, Verapamil, Viloxazine, Warfarin (normal phase), Warfarin (reverse phase), Warfarin (on ULMO CSP), Zopiclone.

Still other examples of chiral compounds include: D-Alaminol, L-Alaminol, L-(+)-Isoleucinol, L-(+)-Isoleucinol, L-(+)-Leucinol, D-Methioninol, L-Methioninol, D-(+)-Phenylalaninol, L-(−)-Phenylalaninol, D-(−)-alpha-Phenylglycinol, L-(+)-alpha-Phenylglycinol, D-(−)-Prolinol, L-(+)-Prolinol, D-Tryptophanol, L-Tryptophanol, D-Valinol, L-Valinol, R-(−)-2-Amino-2-Phenylethanol, BOC-D-Alaminol, BOC-L-Alaminol, CBZ-D-Alaminol, CBZ-L-Alaminol, FMOC-D-Alaminol, FMOC-L-Alaminol, BOC-D-(+)-Isoleucinol, BOC-L-(+)-Isoleucinol, CBZ-D-(+)-Isoleucinol, CBZ-L-(+)-Isoleucinol, BOC-D-(+)-Leucinol, BOC-L-(+)-Leucinol, CBZ-D-(+)-Leucinol, CBZ-L-(+)-Leucinol, BOC-D-Phenylalaninol, BOC-L-Phenylalaninol, CBZ-D-Phenylalaninol, CBZ-L-Phenylalaninol, FMOC-D-Phenylalaninol, FMOC-L-Phenylalaninol, BOC-D-alpha-Phenylglycinol, BOC-L-alpha-Phenylglycinol, FMOC-D-alpha-Phenylglycinol, FMOC-L-alpha-Phenylglycinol, BOC-D-Prolinol, BOC-L-Prolinol, CBZ-D-Prolinol, FMOC-D-Prolinol, FMOC-L-Prolinol, BOC-D-Valinol, BOC-L-Valinol, FMOC-L-Valinol.

Still further examples of chiral compounds include: S-2-methylpiperazine, R-2-methylpiperazine, S-1-Boc-2-methylpiperazine, R-1-Boc-2-methylpiperazine, S-piperazine-2-carboxylic acid, R-piperazine-2-carboxylic acid, S-4-Boc-piperazine-3-carboxylic acid, R-4-Boc-piperazine-3-carboxylic acid, S-4-Boc-2-methylpiperazine, R-4-Boc-2-methylpiperazine, S-4-Boc-piperazine-2-carboxyl-t-Butylamide, R-4-Boc-piperazine-2-carboxyl-t-Butylamide, L-Malic Acid, D-Malic Acid, Diethyl L-(+)-Tartrate, Diethyl D-(−)-Tartrate, S-2-Amino-1-propanol, R-2-Amino-1-propanol, S-1-Amino-2-propanol, R-1-Amino-2-propanol, S-1,2-Decanediol, R-1,2-Decanediol, S-2-Amino-1-butanol, R-2-Amino-1-butanol, S-Octanol, R-Octanol, S-2-Phenylpropylamine, R-2-Phenylpropylamine, S-2-Heptanol, R-2-Heptanol, S-3-Hydroxy-Gamma-Butyrolactone, R-3-Hydroxy-Gamma-Butyrolactone, S-2-Methyl-1-butanol, R-2-Methyl-1-butanol, S-Glyceric acid (hemicalcium salt), R-Glyceric acid (hemicalcium salt), S-1-Benzylglycerol, R-1-Benzylglycerol, S-3-Amino-1,2-propanol, R-3-Amino-1,2-propanol, S-3-Methyl-2-butanol, R-3-Methyl-2-butanol, S-Glycidol, R-Glycidol, S-2-Methyl-1,4-butanediol, R-2-Methyl-1,4-butanediol, S-3-Hydroxyisobutyric acid methyl ester, R-3-Hydroxyisobutyric acid methyl ester, S-2-Methoxy-2-phenylethanol, R-2-Methoxy-2-phenylethanol.

Tartrates, tartrimides, and similar materials, including esters, amides and imides derived from carboxylic acids such as tartaric acid, citric acid, and the like, and the acids themselves may, also be chiral, and so may also be suitable markers for use in the present invention. The markers of the present invention may include an additive represented by Formula I below:

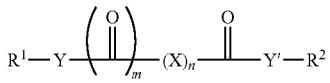

Formula I wherein: Y and Y' are independently —O—, >NH, >NR$^3$, or an imide group formed by taking together both Y and Y' groups and forming a R$^1$—N< group between two >C=O groups; X is independently —Z—O—Z'—, >CH$_2$, >CHR$^4$, >CR$^4$R$^5$, >C(OH)(CO$_2$R$^2$), >C(CO$_2$R$^2$)$_2$, >CHOR$^6$, or >CHCO$_2$R$^2$; Z and Z' are independently >CH$_2$, >CHR$^4$, >CR$^4$R$^5$, >C(OH)(CO$_2$R$^2$), or >CHOR$^6$; n is 0 to 10, or 1 to 8, or 1 to 6, or 2 to 6, or 2 to 4, with the proviso that when n=1, X is not >CH$_2$, and when n=2, both X's are not simultaneously >CH$_2$; m is 0 or 1; R$^1$ is independently hydrogen or a hydrocarbyl group, typically containing 1 to 150, 4 to 30, or 6 to 20, or 10 to 20, or 11 to 18, or 8 to 10 carbon atoms, with the proviso that when R$^1$ is hydrogen, m is 0, and n is more than or equal to 1; R$^2$ is a hydrocarbyl group, typically containing 1 to 150, 4 to 30, or 6 to 20, or 10 to 20, or 11 to 18, or 8 to 10 carbon atoms; R$^3$, R$^4$ and R$^5$ are independently hydrocarbyl groups, hydroxyl-containing groups, or carboxyl-containing groups; and R$^6$ is hydrogen or a hydrocarbyl group, typically containing 1 to 150, or 4 to 30 carbon atoms. In one set of embodiments the hydrocarbyl groups used for R$^1$ and R$^2$ contain at least some portion of branched hydrocarbyl groups.

In one set of embodiments this type of marker is a condensation product of (i), a material represented by formula II and (ii), a mixture comprising a branched alcohol or branched amine having 1 to about 150 carbon atoms, or combinations thereof;

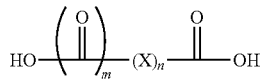

Formula II wherein each X is independently —Z—O—Z—, >CH$_2$, >CR$^1$R$^2$, >C(OH)(CO$_2$R$^2$), or >CHOR$^2$; and wherein each Z is independently >CH$_2$, >CR$^1$R$^2$, >C(OH)(CO$_2$R$^2$), or >CHOR$^2$; m is 0 or 1; n is 1 to 10, with the proviso that when n=1, X is not >CH$_2$, and when n=2, both X's are not >CH$_2$; and each R$^1$ and R$^2$ are independently hydrogen or a hydrocarbyl group.

In one embodiment, within formula II, the X is >CHOR$^2$ and n is 2. In another embodiment, within formula II, (X)n is —CH$_2$—C(OH)(CO$_2$R$^2$)—CH$_2$—. In another embodiment, the m in formula II is 1. In yet other embodiments, component (i) is tartaric acid, citric acid, derivatives of either acid, or combinations thereof.

In one set of embodiments component (ii) comprises a mixture of one or more branched alcohols or amines. In one embodiment, the mixture contains one or more branched alcohols containing 6 to 16 carbon atoms. In another embodiment, the mixture contains branched amines containing 6 to 16 carbon atoms.

In another set of embodiments, alone or in combination with any of the embodiments described above, component (ii) is made up of a mixture of one or more branched alcohols or amines where the overall mixture is at least 25 percent by weight branched, in that at least 25 percent by weight of the alcohols and/or amines making up the mixture have a branched structure.

In some of the embodiments described above, the marker may be represented by the following formulas, or similar versions thereof:

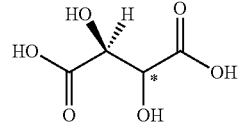

Formula III

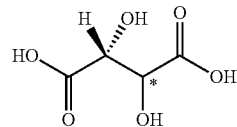

Formula IV where the chiral centers of the molecules are identified by the asterisk (*). There may be more than one chiral center in these molecules, and both carbon atoms located between the —COOH groups in Formula III and Formula IV above may be considered chiral centers. In addition, each of the —OH groups in Formulas III and IV may independently also be an —OR group where R is a hydrocarbyl group.

Markers that fit these categories include tartaric acid derived diesters. The diesters may be derived from tartaric acid and an alcohol and/or a mixture of alcohols (such as Alfol™ 810). Specific examples include D-tartaric acid/Alfol™ 810 diester, L-tartaric acid/Alfol™ 810 diester, D-tartaric acid/Alfol™ 1214 tridecyl alcohol diester, L-tartaric acid/Alfol™ 1214 tridecyl alcohol diester, and mixtures thereof, as long as the mixture is non-racemic, that is, contains an excess of at least one enantiomer.

In some embodiments the markers used in the methods of the invention are selected from the group consisting of tartaric acid and derivatives thereof, glucose and derivatives thereof, 2-bromobutane, D-alaninol, D-ananinol, L-alaninol, L-(+)-isoleucinol, D-leucinol, L-(+)-leucinol, D-methioninol, L-methioninol, D-(+)-phenylalaninol, L-(−)-phenylalaninol, D-(−)-alpha-phenylglycinol, L-(+)-alpha-phenylglycinol, D-(−)-prolinol, L-(+)-prolinol, D-tryptophanol, L-tryptophanol, D-valinol, L-valinol, R-(−)-2-amino-2-phenylethanol, 2-pentanol, 2-fluorobutane, 3-methylhexane, 2-bromomethyl-2-chloromethyl-1-fluoropropane, N-ethyl-N-methyl-N-propylbutan-1-aminium, m-dichlorocyclohexane and o-dichlorocyclohexane, amino(hydroxy)acetic acid, 1-aminoethanol, 2-[pyridine-3-yl(pyridine-4-yl)methyl]pyridine, 2-amino-2-hydroxy-3-oxoacetic acid, and combinations thereof.

In other embodiments the markers used in the methods of the invention are selected from the group consisting of cholesteryl acetate, D-tartaric acid/Alfol 810 diester, L-tartaric acid/Alfol 810 diester, L-menthyl lactate, S-(−)-perillaldehyde, 1R-(−)-menthyl acetate, R-(+)-limonene, L-tartaric acid/Alfol 1214 tridecyl alcohol diester, and combinations thereof with the proviso that the mixture used is non-racemic in regards to at least one marker.

In still other embodiments: where the fluid involved is a passenger car motor oil, the marker may be cholesteryl acetate, L-menthyl lactate, S-(−)-perillaldehyde, 1R-(−)-menthyl acetate, R-(+)-limonene, and combinations thereof where the fluid is a heavy duty diesel engine oil, the marker may be S-(−)-perillaldehyde, 1R-(−)-menthyl acetate, R-(+)-limonene and combinations thereof; where the fluid is a automatic transmission fluid, the marker may be cholesteryl acetate, S-(−)-perillaldehyde, 1R-(−)-menthyl acetate, R-(+)-limonene, and combinations thereof; where the fluid is a gear oil, the marker may be L-menthyl lactate, 1R-(−)-menthyl acetate, R-(+)-limonene, and combinations thereof; where the fluid is a hydraulic fluid, the marker may be L-menthyl lactate, 1R-(−)-menthyl acetate, R-(+)-limonene, and combinations thereof; where the fluid is diesel fuel, marker may be cholesteryl acetate, L-menthyl lactate, S-(−)-perillaldehyde, 1R-(−)-menthyl acetate, R-(+)-limonene, and combinations thereof; and where the fluid is gasoline, the marker may be L-menthyl lactate, 1R-(−)-menthyl acetate, R-(+)-limonene, and combinations thereof.

In some embodiment the markers of the present invention provide a measurable impact on the optical rotation caused by the fluid in which it is used. In some embodiments this impact is more than the margin of error of the testing method used. In other embodiments the marker causes the optical rotation caused by the fluid to change by at least 5%, at least 50% or at least 100%.

When present, the amount of marker present in the fluid is not overly limited as long as there is enough marker to allow for positive identification and so long as there is not so much marker that it interferes with the performance and/or desired characteristics of the fluid. The markers may be present in the fluid at concentrations of 10 to 10,000 ppm or 10 to 1,000 ppm. In another embodiment the makers are present in the fluid at 20 to 500 ppm; 25 to 350 ppm, 30 to 130 ppm; or to 100 ppm. In other embodiments the markers are present in the fluid at concentrations from 0.05 to 10% wt, or from 0.1 to 10% wt, or from 0.5 to 10% wt. In still other embodiments the markers are present at more than 0.05% wt, or more than 0.1% wt.

The marker compound itself may be soluble in water, substantially soluble in water, substantially insoluble in water or insoluble in water. In other embodiments the marker compound is soluble in organic liquids, such as oil, substantially soluble in organic liquids, substantially insoluble in organic liquids or insoluble in organic liquids. The marker compound should be substantially soluble and/or soluble in the fluid with which it is used, or substantially soluble and/or soluble in at least one of the components present in the fluid with which it is used.

The optical markers of the present invention may be used in combination with other markers including non-optically active markers such as markers that react with reagents to provide positive identification of a fluid. The use of multiple types of markers allows for additional levels of protection and accuracy when verifying the identity and/or source of the fluid being tested.

In another embodiment, the marker compound is added to a functional fluid where the marker is in the form of a concentrate containing a mixture of the marker compound and a polymeric compound. This polymeric compound may be one or more conventional additives for functional fluids. In one embodiment the polymeric compounds that may be in the concentrate include dispersants, detergents, antiwear agents, friction modifiers, metal deactivators, corrosion inhibitors, seal swell agents, viscosity modifiers, pour point depressants, thickeners, and antioxidants, either alone or in combinations with one another.

Optional Components

Optional components may be added to the marker solutions or the fluids. These include, for example, surfactants, maskants and fragrances to improve customer appeal, as well as antifoam additives to improve product manufacture and use. These optional components can be used with in the marker solutions either alone or in combination.

The optional component may be used in the range of about 0% to about 20% wt, in one embodiment about 0.01% to about 5% wt, and in another embodiment about 0.1% to about 2% wt of the reagent solution.

Method

The present invention includes a method to determine the identity of a fluid comprising: (1) adding an optional marker component to a fluid; (2) obtaining a sample of the fluid before, during or after the fluid's use; (3) passing a beam of polarized light through the sample; (4) analyze the results by measuring the rotation of the plane of polarized light after it passes through the sample; (5) determining and/or verifying the identity of the fluid. In some embodiments the optical rotation observed is that caused by the fluid itself without the addition of the optional optical markers described herein. In other embodiments one or more of the optically active markers described above are added to the fluid, which causes at least some of the rotation observed in the fluid.

In one embodiment the fluid is used in an application and the marker survives the conditions of the use such that it still allows for the identification of the fluid after such use. Such uses include the use of a functional fluid, such as a lubricant, in a device, such as an engine, while the device is operating. Including the exposure of the fluid to extreme temperatures, extreme pressures, moving parts and shear, or combinations thereof.

It is not necessary that the sample be taken during actual operation of the engine or other device or machinery in order to obtain a representative sample of the fluid. The sample of fluid may be taken at any time before, during and/or after operation of the engine or equipment or device. The fluid sample can be new, used or combinations thereof. In one embodiment the fluid test is especially useful during and/or after operation for some period of time.

Diagnostic Kit

The diagnostic kit includes a means to generate a polarized beam of light and to direct that light beam through a sample of fluid. The kit further includes a means for measuring the rotation of the beam and/or plane of polarized light after it passes through the sample of fluid, compared to the beam before it passes through the sample. The measurement of the amount of rotation the plane of the polarized light beam experiences, is the means for identifying the fluid being tested.

In one embodiment the present invention excludes the use of reactive markers or reactive reagents where a marker-containing sample of fluid is reacted with a reagent in order to produce an observable response used to identify the fluid.

In one embodiment the present invention excludes identification by observing a compound removed from the function fluid by a water extraction. A water extraction includes where a compound, such as a dye, in a functional fluid is removed from the functional fluid and drawn into an aqueous solution, due to the compound's miscibility in water. The observance of the compound, without any reaction taking place, in the water solution is the only indicator provided.

In one embodiment the functional fluid is an engine oil. The engine oil sample, or other functional fluid to be tested, may be obtained using a dipstick provided as a part of the engine, transmission or other equipment under lubrication. The user will withdraw an amount of oil along with the dipstick or other device, which may then be transferred to a sample container where the sample container is glass or some other material that allows light to pass through it. The amount of fluid necessary for testing depends on the polarimeter used, and is some embodiments may be as small as a single drop, or as large as a several milliliters, or even several hundred milliliters. Once the sample has been placed on the sample container, the beam of polarized light may be aimed through the sample and the measurement of the rotation of the light beam may be observed. The user may refer to a guide and/or visual indicia to help interpret the observed rotation and make a determination as the fluid's identity, condition and/or source.

The marking/identification of a fluid is desirable because counterfeiting and adulteration/dilution of genuine fluids is a large concern of fluid suppliers as counterfeiting and adulteration results in a loss of profits, customer complaints, and harm to brand name and reputation. A simple, easy to use marker system is beneficial since different fluids can be indistinguishable based on casual inspection. Chemical analyses or physical properties can tell various fluids apart but these analyses require expensive laboratory test equipment and often take too long to be a practical end user identification test. The disclosed methods enable end users to exclude a counterfeit or adulterated product based on optical rotation, in an efficient and convenient way.

Visual Indicia

Analysis of the test sample can be accomplished by visual inspection of the light beam rotation, and may include using a provided visual indicia as a guide.

The visual indicia may include an artistic rendering, a reproduction of a photograph of one or more functional fluids in various conditions with and without the reagent. The visual indicia generally include one representation, two representations or more than two representations of one or more functional fluids and/or a diagram showing the expected light beam, rotation for a fluid of a given source, a given identity, and/or a given condition. In one embodiment the preferred visual indicia is one or more representations showing a positive identification result and one or more representations showing a negative identification result. A descriptive text corresponding to each of these examples may be provided. It is to be understood that a different number of indicia may be provided.

SPECIFIC EMBODIMENT

The following data was collected with a JASCO Model DIP-360 digital polarimeter, which was operated according to the manufacturer's directions. 100 mm length test cells were used for all testing.

Example 1

Four fully formulated, commercially available engine oils are treated with several optically active markers and tested using a polarimeter. The results are summarized in the table below.

TABLE 1

| Engine Oil Data | | | | | |
|---|---|---|---|---|---|
| Marker[1] | Conc | Oil A[2] | Oil B[2] | Oil C[2] | Oil D[2] |
| None - Oil Alone | 0% wt | 0.150* | 0.084* | −0.619* | 0.114* |
| Cholesteryl Acetate | 10% wt | −3.650 | | | |
|  | 1% wt |  | Insoluble |  | Insoluble |
|  | 0.5% wt | −1.701 | Insoluble |  | Insoluble |
|  | 0.1% wt | −0.154 | Insoluble |  |  |
|  | 0.05% wt | −0.021 | Insoluble |  |  |
| DL-tartaric acid/ | 10% wt | 0.220 | | | |
| Alfol 810 diester[3] | 1% wt | 0.374* | Insoluble | −0.094* | Insoluble |
|  | 0.5% wt | 0.201* | Insoluble | 0.374* | 0.143* |
|  | 0.1% wt | 0.118* | 0.035* |  |  |
|  | 0.05% wt | −0.052* | 0.081* |  |  |
| L-menthyl lactate | 10% wt | −4.600 | | | |
|  | 1% wt |  | −3.193* | −0.436* | Insoluble |
|  | 0.5% wt |  | −2.781* | 0.464* | Insoluble |
|  | 0.1% wt | −0.445* | −0.719* |  |  |
|  | 0.05% wt | −0.166* | −0.271* |  |  |
| S-(−)-perillaldehyde | 10% wt | −11.690 | | | |
|  | 1% wt |  | −10.622* |  | −11.887* |
|  | 0.5% wt |  | −5.728* |  | Insoluble |
|  | 0.1% wt |  | −1.221* |  |  |
|  | 0.05% wt | −0.061* |  |  |  |
| 1R-(−)-menthyl acetate | 10% wt | −6.580 | | | |
|  | 1% wt | −7.144* | −5.515* | −0.065* | −6.574* |
|  | 0.5% wt | −2.781* | −3.978* | 0.111* | −3.994* |
|  | 0.1% wt |  |  |  |  |
|  | 0.05% wt |  |  |  |  |

TABLE 1-continued

Engine Oil Data

| Marker[1] | Conc | Oil A[2] | Oil B[2] | Oil C[2] | Oil D[2] |
|---|---|---|---|---|---|
| R-(+)-limonene | 10% wt | 11.130 | | | |
| | 1% wt | | | −0.860* | 12.695* |
| | 0.5% wt | | | 0.362* | 6.416 |
| | 0.1% wt | | 1.903* | | |
| | 0.05% wt | 0.250* | 0.595* | | |
| Cholesterol | 10% wt | Insoluble | | | |
| | 1% wt | Insoluble | Insoluble | Insoluble | Insoluble |
| | 0.5% wt | Insoluble | Insoluble | Insoluble | Insoluble |
| | 0.1% wt | Insoluble | Insoluble | | |
| | 0.05% wt | Insoluble | Insoluble | | |
| L-tartaric acid/Alfol 1214 tridecyl alcohol diester | 10% wt | Insoluble | | | |
| | 1% wt | Insoluble | Insoluble | Insoluble | Insoluble |
| | 0.5% wt | Insoluble | Insoluble | Insoluble | Insoluble |
| | 0.1% wt | Insoluble | Insoluble | | |
| | 0.05% wt | Insoluble | Insoluble | | |

[1]All reported test values marked with an * are averages of 2 to 5 results. All other reported values are single test results. Blanks indicate no sample was prepared at that concentration level.
[2]Oil A is unused Valvoline ™ motor oil. Oil B is unused Mobil 1 ™ motor oil. Oil C is used Valvoline ™ motor oil which was drained from a car engine after 3700 miles. Oil D is a Rotella ™ heavey duty engine oil.
[3]The marker is a mixture of the D and L enantiomers with a small excess of one enantiomer.

Example 2

Four fully formulated, commercially available functional fluids are treated with several optically active markers and tested using a polarimeter. The results are summarized in the table below.

TABLE 2

Functional Fluid Data

| Marker[1] | Conc | Fluid A[2] | Fluid B[2] | Fluid C[2] | Fluid D[2] |
|---|---|---|---|---|---|
| None - Fluid Alone | 0% wt | −0.262* | −0.212* | −0.041* | 1.005* |
| Cholesteryl Acetate | 10% wt | −3.56 | | | |
| | 1% wt | | | | |
| | 0.5% wt | | | | |
| DL-tartaric acid/ Alfol 810 diester[3] | 10% wt | −1.0 to 1.0 | | | |
| | 1% wt | | −0.085* | −0.058* | 0.328* |
| | 0.5% wt | −0.412* | −0.257* | 0.086* | 0.981* |
| L-menthyl lactate | 10% wt | 1.0 to 2.1 | | | |
| | 1% wt | | 0.262* | −3.282* | −2.876* |
| | 0.5% wt | | −0.695* | −1.826* | −3.146* |
| S-(−)-perillaldehyde | 10% wt | −11.24 | | | |
| | 1% wt | | | | |
| | 0.5% wt | | | | |
| 1R-(−)-menthyl acetate | 10% wt | −6.56 | | | |
| | 1% wt | | −0.107* | −5.000* | −6.295* |
| | 0.5% wt | −0.412* | 1.273* | −3.328* | −2.515* |
| R-(+)-limonene | 10% wt | 10.22 | | | |
| | 1% wt | | −0.422* | 9.067* | 11.581* |
| | 0.5% wt | 0.588* | −0.010* | 5.512* | 6.201* |
| Cholesterol | 10% wt | Insoluble | | | |
| | 1% wt | | | | |
| | 0.5% wt | Insoluble | | | |
| L-tartaric acid/Alfol 1214 tridecyl alcohol diester | 10% wt | Insoluble | | | |
| | 1% wt | −3.151* | | | |
| | 0.5% wt | | | | |

[1]All reported test values marked with an * are averages of 2 to 5 results. All other reported values are single test results. Blanks indicate no sample was prepared at that concentration level.
[2]Fluid A is an unused automatic transmission fluid. Fluid B is a used automatic transmission fluid drain after 155,000 miles. Fluid C is a gear oil. Fluid D is a hydraulic fluid.
[3]The marker is a mixture of the D and L enantiomers with a small excess of one enantiomer.

Example 3

Two commercially available fuels are treated with several optically active markers and tested using a polarimeter. The results are summarized in the table below.

TABLE 3

Fuel Data

| Marker[1] | Conc | Fuel A[2] | Fuel B[2] |
|---|---|---|---|
| None - Fluid Alone | 0% wt | 0.042* | 0.002* |
| Cholesteryl Acetate | 1% wt | −3.358* | |
| | 0.5% wt | −1.545* | |
| | 0.1% wt | −0.312* | |
| | 0.05% wt | −0.106* | |
| DL-tartaric acid/Alfol 810 diester[3] | 1% wt | | |
| | 0.5% wt | | 0.343* |
| | 0.1% wt | | |
| | 0.05% wt | | |
| L-menthyl lactate | 1% wt | −6.718* | −6.589* |
| | 0.5% wt | | −3.602* |
| | 0.1% wt | −0.643* | |
| | 0.05% wt | −0.296* | |
| S-(−)-perillaldehyde | 1% wt | −11.651* | |
| | 0.5% wt | −5.629* | |
| | 0.1% wt | −0.991* | |
| | 0.05% wt | −0.502* | |
| 1R-(−)-menthyl acetate | 1% wt | −6.252* | |
| | 0.5% wt | −3.266* | −3.391* |
| | 0.1% wt | −0.672* | |
| | 0.05% wt | | |
| R-(+)-limonene | 1% wt | 10.593* | |
| | 0.5% wt | 6.183* | 5.447* |
| | 0.1% wt | 0.992* | |
| | 0.05% wt | 0.565* | |
| Cholesterol | 1% wt | Insoluble | |
| | 0.5% wt | Insoluble | |
| | 0.1% wt | Insoluble | |
| | 0.05% wt | Insoluble | |
| L-tartaric acid/Alfol 1214 tridecyl alcohol diester | 1% wt | Insoluble | |
| | 0.5% wt | Insoluble | |
| | 0.1% wt | Insoluble | |
| | 0.05% wt | Insoluble | |

[1]All reported test values marked with an * are averages of 2 to 5 results. All other reported values are single test results. Blanks indicate no sample was prepared at that concentration level.
[2]Fuel A is a commercially available diesel fuel. Fuel B is a commercially available gasoline.
[3]The marker is a mixture of the D and L enantiomers with a small excess of one enantiomer.

The results show that some fluids provide a measurable amount of optical rotation that may be used in the methods of the invention as a means of identifying and/or verifying the identity of the fluid. The results also show that the optically active markers defined above may be used in such fluids to adjust, impact, and/or change the amount of optical rotation caused by the fluid, which may make it easier to identify a fluid. The markers may also be used to achieve an amount of rotation that would not otherwise be present in such a fluid, thus providing a convenient means of identifying and/or verifying the identity of a fluid.

While the invention has been explained, it is to be understood that various modifications thereof will become apparent to those skilled in the art upon reading the specification. Therefore, it is to be understood that the invention disclosed herein is intended to cover such modifications as fall within the scope of the appended claims.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word about. Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. Unless otherwise indicated, all percentage values are percents by weight. It is to be understood that the upper and lower amounts, ranges, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

We claim:

1. A method to determine the identity of an organic functional fluid comprising:
   (1) adding an optically active marker component to an organic functional fluid;
   (2) obtaining a sample of the fluid before, during or after its use in an application;
   (3) passing a beam of polarized light through the sample of fluid;
   (4) measuring the rotation of the plane of the light after it passes through the sample of fluid by comparing it to the light's original orientation;
   (5) determining the identity of the fluid by the amount of rotation observed;
   wherein the optically active marker component comprises a compound of the formula:

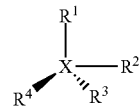

wherein X is C, N, P, or S; and $R^1$, $R^2$, $R^3$, and $R^4$ are each independently a hydrocarbyl group, an $-OR^5$ group where $R^5$ is a hydrogen or a hydrocarbyl group, an aromatic group, a lone pair of electrons when X is N, a double bonded Oxygen atom when X is P or S, with the proviso that none of the R groups are identical, wherein the optically active marker component is non-racemic in regards to at least one set of enantiomers.

2. The method of claim 1 wherein the optically active marker component comprises a chiral molecule that is at least partially soluble in the organic functional fluid.

3. The method of claim 1 wherein the fluid is selected from the group consisting of automatic transmission fluids, engine oils, traction drive transmission fluids, manual transmission fluids, power steering fluids, antifreeze fluids, lubricating oils, greases, crankcase lubricants, mineral oils, oils with Group 1, 2, 3 or 4 base oils, differential lubricants, turbine lubricants, gear lubricants, gear box lubricants, axle lubricants, brake fluids, farm tractor fluids, transformer fluids, compressor fluids, cooling system fluids, metal working fluids, hydraulic fluids, industrial fluids, passenger car fuels, diesel engine fuels, bio-based fuels, continuously variable transmission fluid, infinitely variable transmission fluids, and mixtures thereof.

4. The method of claim 1 wherein the marker component is added to the fluid before or during the fluid's use in an application.

5. The method of claim 1 wherein the concentration of the marker component in the in the functional fluid is from 10 to 1000 ppm.

6. The method of claim 1 wherein the optically active marker component comprises cholesteryl acetate, one or more tartaric acid derived diesters and/or imides, L-menthyl lactate, (S)-(−)-perillaldehyde, (1R)-(−)-menthyl acetate, (R)-(+)-limonene, cholesterol, sucrose, camphor, penicillin V, taxol, bromobutane, cavicularin, or combinations thereof.

* * * * *